US 11,079,364 B2

(12) United States Patent
Leger et al.

(10) Patent No.: US 11,079,364 B2
(45) Date of Patent: Aug. 3, 2021

(54) CALIBRATION OF AN AIR QUALITY SENSOR IN A DEVICE

(71) Applicant: WITHINGS, Issy les Moulineaux (FR)

(72) Inventors: Charlotte Leger, Montrouge (FR); Charlotte Bessis, Paris (FR); Ianis Oueslati, Vanves (FR); Marc Besnard, Paris (FR)

(73) Assignee: Withings, Issy les Moulineaux (FR)

( * ) Notice: Subject to any disclaimer, the term of this patent is extended or adjusted under 35 U.S.C. 154(b) by 125 days.

(21) Appl. No.: 16/182,213

(22) Filed: Nov. 6, 2018

(65) Prior Publication Data
US 2020/0141913 A1    May 7, 2020

(51) Int. Cl.
*G01N 33/00*  (2006.01)
*G04G 21/02*  (2010.01)

(52) U.S. Cl.
CPC ..... *G01N 33/0006* (2013.01); *G01N 33/0027* (2013.01); *G01N 33/0063* (2013.01); *G04G 21/02* (2013.01)

(58) Field of Classification Search
CPC ........... G01N 33/0006; G01N 33/0027; G01N 33/0063; G01N 27/4175; G01N 3/62; G01N 2030/626; G04G 21/02
USPC ... 73/1.06, 1.07, 31.01, 31.02, 31.05, 31.06; 204/157.3, 424–429
See application file for complete search history.

(56) References Cited

U.S. PATENT DOCUMENTS

| | | | |
|---|---|---|---|
| 4,489,590 A * | 12/1984 | Hadden | G01N 33/0006 73/1.04 |
| 4,590,789 A | 5/1986 | Kunze | |
| 5,206,511 A * | 4/1993 | Apperson | G01N 21/274 250/252.1 |
| 6,774,613 B1 | 8/2004 | Becker et al. | |
| 2011/0154881 A1* | 6/2011 | Ascheman | G01N 31/22 73/1.06 |
| 2011/0197649 A1 | 8/2011 | Han et al. | |
| 2013/0276508 A1* | 10/2013 | Eastman | G01N 21/77 73/1.06 |
| 2014/0277624 A1 | 9/2014 | Pariseau et al. | |
| 2015/0238141 A1 | 8/2015 | Lai | |
| 2017/0351221 A1 | 12/2017 | Balti et al. | |

FOREIGN PATENT DOCUMENTS

| | | |
|---|---|---|
| CN | 204 009 395 U | 12/2014 |
| CN | 204 086 834 U | 1/2015 |
| KR | 101 598 908 B1 | 3/2016 |
| WO | WO 2015160830 A1 | 10/2015 |
| WO | WO 2017/207594 A1 | 12/2017 |

* cited by examiner

*Primary Examiner* — Robert R Raevis
(74) *Attorney, Agent, or Firm* — von Briesen & Roper, s.c.

(57) ABSTRACT

A device (1) comprising a cavity (5) defining an internal volume, an air quality sensor (9) being adapted to measure a concentration of at least one air compound present in the internal volume, the cavity (5) can be alternatively in:

an open state in which air can enter into the cavity (5) from the outside of the cavity (5), and a closed state in which no air can circulate between the outside and the inside of the cavity (5), the air quality sensor (9) being adapted to be calibrated when the cavity (5) is in the closed state and once the internal volume no longer comprises the air compound or comprises a concentration of the air compound that is below a predefined threshold.

15 Claims, 8 Drawing Sheets

CALIBRATION OF AN AIR QUALITY SENSOR IN A DEVICE

FIELD OF THE DISCLOSURE

The present disclosure concerns a device, for example a wearable device such as a wrist watch or an activity tracker, with an air quality sensor.

BACKGROUND OF THE DISCLOSURE

It is known to embed an air quality sensor into a device like a wrist watch.

The air quality sensor can detect and monitor the presence of air pollution in a surrounding area, for both indoor and outdoor environments. It can provide useful information to a user on the air quality that may negatively impact his health, and cause harmful effects such as cold symptoms or respiratory diseases.

In such a device, the air quality sensor can produce an electric current according to a concentration level of some compounds present in the air.

However, the electrical current may also vary according to other parameters, such as humidity, temperature and aging of other components constitutive of the device which may release gas affecting the accuracy of the air quality sensor located nearby.

It is therefore necessary to recalibrate the sensor on a regular basis. In the absence of recalibration, the air quality sensor is likely to output inaccurate measures that may mislead the user.

However, calibration process is usually difficult and burdensome to implement for a user.

Therefore, there remains a need to provide a device with an air quality sensor able to provide reliable air quality measurements, whatever its conditions of use, and that remains easy to use in the context of everyday life.

SUMMARY OF THE DISCLOSURE

The present disclosure relates to a device comprising a cavity defining an internal volume, an air quality sensor being adapted to measure a concentration of at least one air compound present in the internal volume. The cavity can be alternatively in:
- an open state in which air can enter into the cavity from the outside of the cavity, and
- a closed state in which no air can circulate between the outside and the inside of the cavity, the air quality sensor being adapted to be calibrated when the cavity is in the closed state once the internal volume no longer comprises the air compound or comprises a concentration of the air compound that is below a predefined threshold.

Thanks to these dispositions, it is possible to perform a reliable measurement of the air compound.

In various embodiments according to the present disclosure, use may also possibly be made of one and/or the other of the following dispositions, taken separately or in combination, according to which:
- the cavity comprises an opening so that air can exclusively enter the cavity through the opening, the cavity being elsewhere isolated from the device;
- the air quality sensor is adapted to produce an electric current by consuming the air compound present in the internal volume of the cavity,
- the air compound is $NO_2$,
- the internal volume of the cavity is less than $0.3 \text{ cm}^3$, less than $0.2 \text{ cm}^3$, less than $0.1 \text{ cm}^3$, or even less than $0.05 \text{ cm}^3$;
- the cavity comprises a first grid and a second grid, the second grid being adapted to move relative to the first grid so that the cavity can be in the open state or in the closed state;
- each of the first and second grids comprises a plurality of through apertures, wherein at least some of the through apertures of the first and second grids face each other when the cavity is in the open state and wherein the through apertures of the first and second grids are offset to one another when the cavity is in the closed state;
- the cavity comprises a door, the door being adapted to move relative to the opening so that the cavity can be in the open state or in the closed state;
- the device comprises an accelerometer adapted to detect a movement of the user, the air quality sensor being adapted to be calibrated when the accelerometer does no detect any movement of the user;
- the cavity comprises a hole, the air quality sensor being located into the hole, the cavity and the air quality sensor being sealed together in an airtight manner by using at least one gasket; and
- the device is a wearable device, such as a watch.

The present disclosure also relates to a method for calibrating an air quality device of a device as disclosed, comprising at least the steps of:
- switching the cavity from the open state to the closed state;
- waiting for the internal volume to no longer comprise the air compound or to comprise a concentration of the air compound that is below a predefined threshold; and
- calibrating the air quality sensor.

BRIEF DESCRIPTION OF THE DRAWINGS

Other features of the disclosure appear from the following detailed description, given by way of non-limiting example, and with reference to the accompanying drawings, in which.

In the figures, the same references denote identical or similar elements.

DETAILED DESCRIPTION OF THE DISCLOSURE

Device

Figure 1:
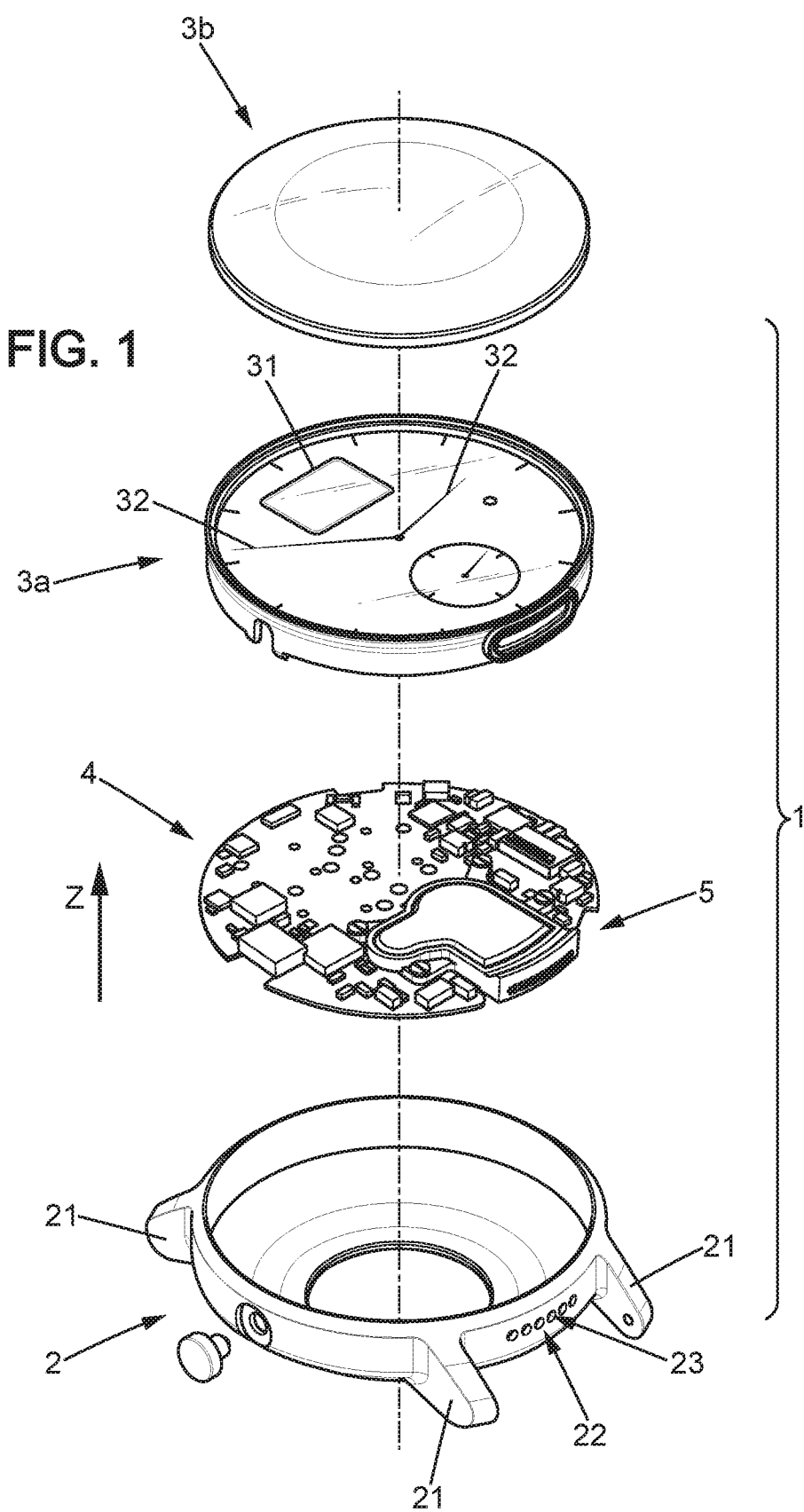
FIG. 1 shows an exploded view of the device according to the present disclosure.

FIG. 1 shows a device 1 according to the present disclosure.

The device 1 can be a wearable device, such as a watch, a wrist watch or an activity tracker.

However, the device 1 can also be any other device, such as glasses, a necklace, a ring, a weight scale, etc.

As illustrated on FIG. 1, the device 1 may comprise a casing 2, a dial plate 3a and a top cover 3b of the dial plate 3a. The casing 2, the dial plate 3a and the top cover 3b are arranged one on top of another in a vertical direction Z. The thickness of the device 1 is thus defined along this vertical direction Z.

The device 1 can be a digital watch, such that the dial plate 3a comprises a display 31. As a variant or complementarily, the device 1 may be an analog type watch, such that the dial plate 3a comprises stick-like hands 32 with a traditional clock face for instance.

To be attached to a wrist of a user, the casing 2 may comprise projections 21 for attachment to a wristband (not illustrated) as known per se and thus not described in more details.

As illustrated on FIG. 1, the device 1 can have a round shape. However, other shapes, such as square or rectangle, are also possible. Similarly, the device 1 can be relatively small, as for a watch for example, or can have bigger dimensions when it comes to objects having larger dimensions, as for a weight scale for another example.

Figure 2:
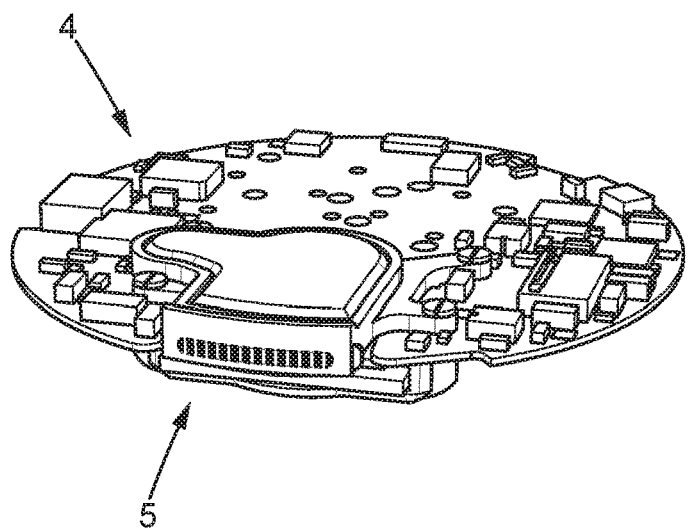
FIG. 2 shows a perspective view of an internal part of the device of FIG. 1 according to a first embodiment.

The device 1 also comprises an internal part 4 illustrated on FIG. 2. As illustrated on FIG. 1, the internal part 4 can be sandwiched between the casing 2 and the dial plate 3a.

Figure 4:
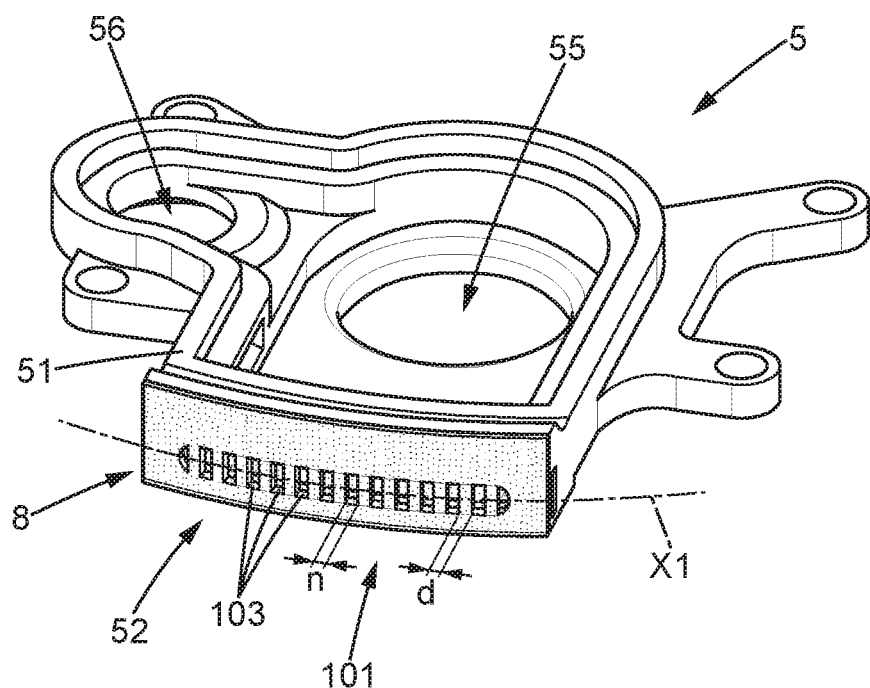
FIG. 4 shows a perspective view of a cavity of the internal part of FIGS. 2 and 3, the cavity comprising a first grid.
Figure 9:
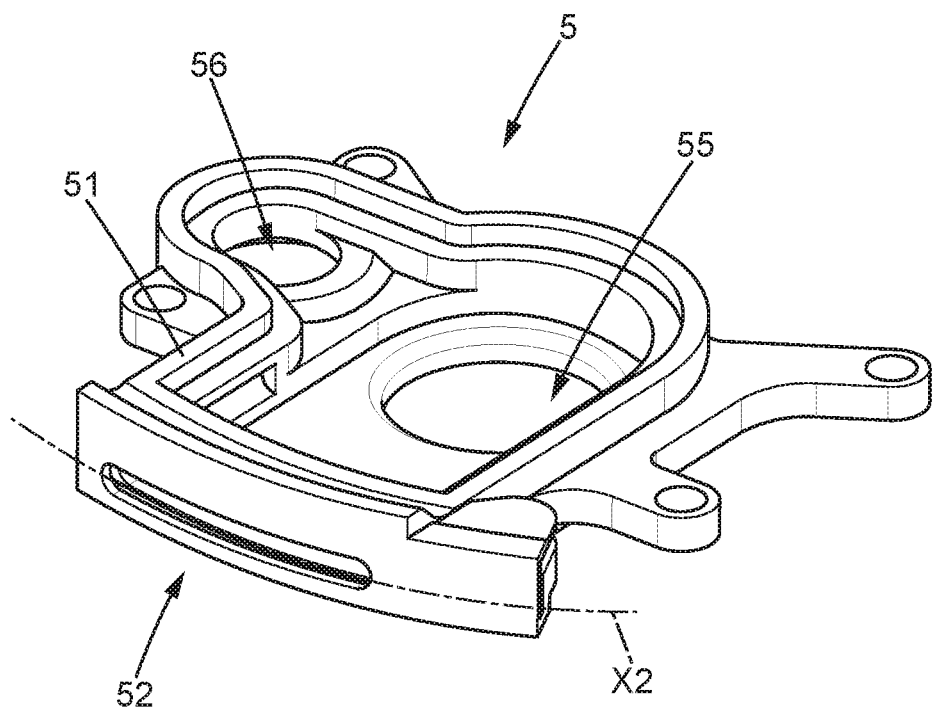
FIG. 9 shows a perspective view of a cavity of the internal part of FIG. 8.
Figure 10:
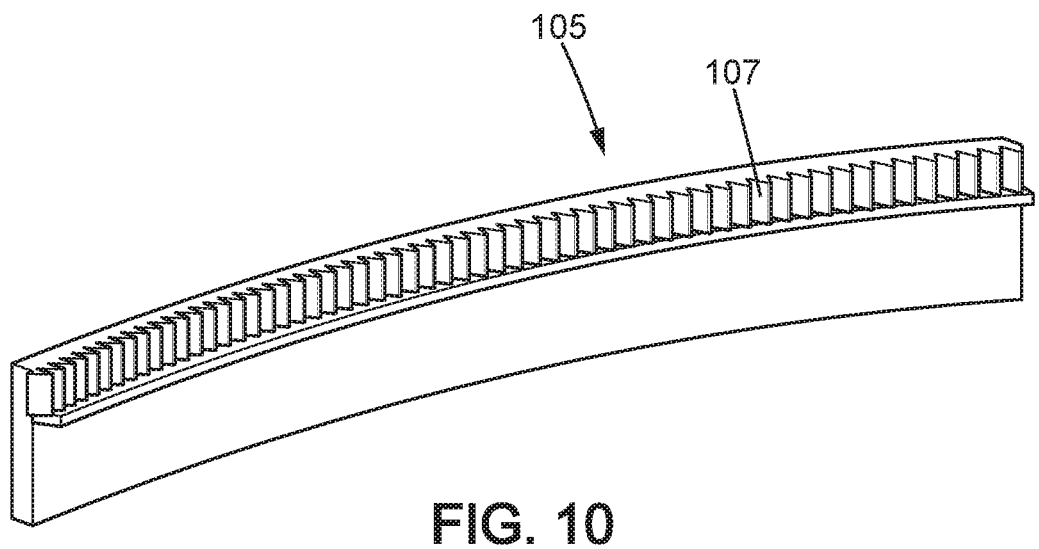
FIG. 10 shows front view of a door according to the second embodiment.

As illustrated more particularly on FIGS. 4 and 9, the internal part 4 comprises a cavity 5. The cavity 5 may be molded, in particular as a single piece.

The cavity 5 comprises a wall 51 and an opening 52.

The wall 51 forms at least the lateral portion of the cavity 5.

The cavity 5 also comprises a bottom portion 53 and a top portion 54.

The bottom portion 53 can comprise a first hole 55 and a second hole 56. As illustrated on FIGS. 4 and 9, the holes 55, 56 can have a circular shape.

The top portion 54 can be closed by a cover 6.

The cavity 5 defines and delimits an internal volume. The internal volume is suited and intended to receive an air volume coming from the outside of the cavity 5, and more precisely from the outside of the device 1, through the opening 52. The cavity 5 may take any form, notably cylindrical, parallelepipedal or other so as to form the internal volume.

The terms "internal", "inside" and "external", "outside" when applied to the cavity 5 reflect the fact that the cavity 5 delimits the internal volume comprising a quantifiable amount of air, distinguishable from the air present in the surrounding of the device 1 or present elsewhere in the device 1. It is therefore with reference to this situation that these terms should be understood.

The cavity 5 can be arranged on, or fixed to, a printed circuit board 7. The printed circuit board 7 can comprise a control unit, an oscillator, a battery either conventional or rechargeable (not illustrated), or any known elements for the functioning of the device 1.

In order for the internal volume of the cavity 5 to be in fluid communication with the outside of the device 1, the casing 2 can comprise a perforated area 22, wherein through bores 23 opens on the cavity 5 and the outside of the device 1.

The through bores 23 may be aligned in the perforated area 22, facing the opening 52 of the cavity 5.

As illustrated on FIG. 1, the casing 2 comprises six through bores 23. Each through bore 23 may have a diameter comprised between 0.5 mm (millimeter) and 1.5 mm, for example about 1 mm.

In an embodiment, the device 1 can also comprise a membrane 8 which is impermeable to water but permeable to air. The water-impermeable membrane 8 is placed facing the opening 52 so that air entering the cavity 5 passes through the membrane 8.

As illustrated more particularly on FIGS. 3, 4, 6 and 7, the water-impermeable membrane 8 can be placed in front of the opening 52 toward the outside of the cavity 5.

As a variant, the water-impermeable membrane 8 may as well be inside the cavity 5 on the inside face of the opening 52.

As another variant, the water-impermeable membrane 8 may also be placed on the internal or external side of the perforated area 22. This way, the water-impermeable membrane 8 can ensure that the whole device 1 is waterproof.

The water-impermeable membrane 8 prevents the ingress of water inside the cavity 5. This way, the user can for example immerse briefly the device 1 in water without any damage.

The water-impermeable membrane 8 may be formed as a thin wall manufactured in synthetic material having a microporous structure.

Air Quality Sensor

The device 1 comprises an air quality sensor 9. The air quality sensor 9 is arranged in the cavity 5 of the internal part 4.

"The air quality sensor is arranged in the cavity" means that the air quality sensor 9 is located inside, opens on, or is at least is in fluid communication with the internal volume of the cavity 5.

Figure 3:
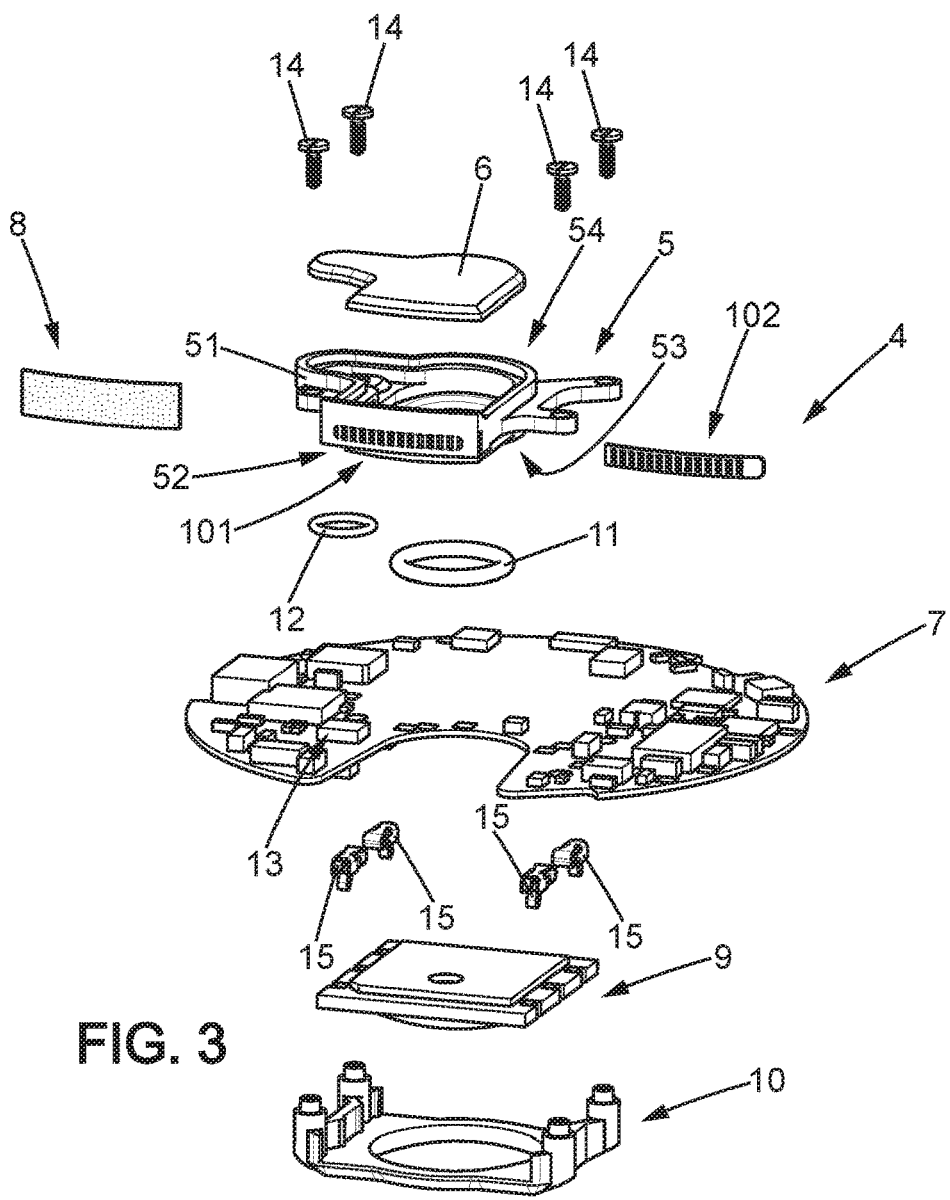
FIG. 3 shows an exploded view of the internal part of FIG. 2.

More particularly, as illustrated on FIG. 3, the air quality sensor 9 is placed in the first hole 55 of the cavity 5. This way, the air quality sensor 9 is in direct contact with the air present in the internal volume of the cavity 5.

The air quality sensor 9 is sealed with the cavity 5 in an airtight manner with a gasket 11. To ensure that the air quality sensor 9 is sealed with the cavity 5, the device 1 can comprise a supporting element 10. The supporting element 10 holds the air quality sensor 9 against the cavity 5.

More precisely, the cavity 5 can be fixedly attached to the supporting element 10. As illustrated on FIGS. 3 and 8, the device 1 may comprise screws 14 that go through the cavity 5 and the printed circuit board 7 and that are fixed to the supporting element 10.

Spring elements 15 are compressed between the printed circuit board 7 and the air quality sensor 9. The spring elements 15 can be electrical conductors that ensure electrical contact between the air quality sensor 9 and the printed circuit board 7.

As a variant, to ensure that the air quality sensor 9 is sealed with the cavity 5, the air quality sensor 9 may be soldered to the printed circuit board 7 and the cavity 5 may be screwed on the printed circuit board 7, thus compressing the gasket 11.

The device 1 can also comprise other types of sensors, such as a temperature sensor, a humidity sensor, a pressure sensor, or the like.

Figure 8:
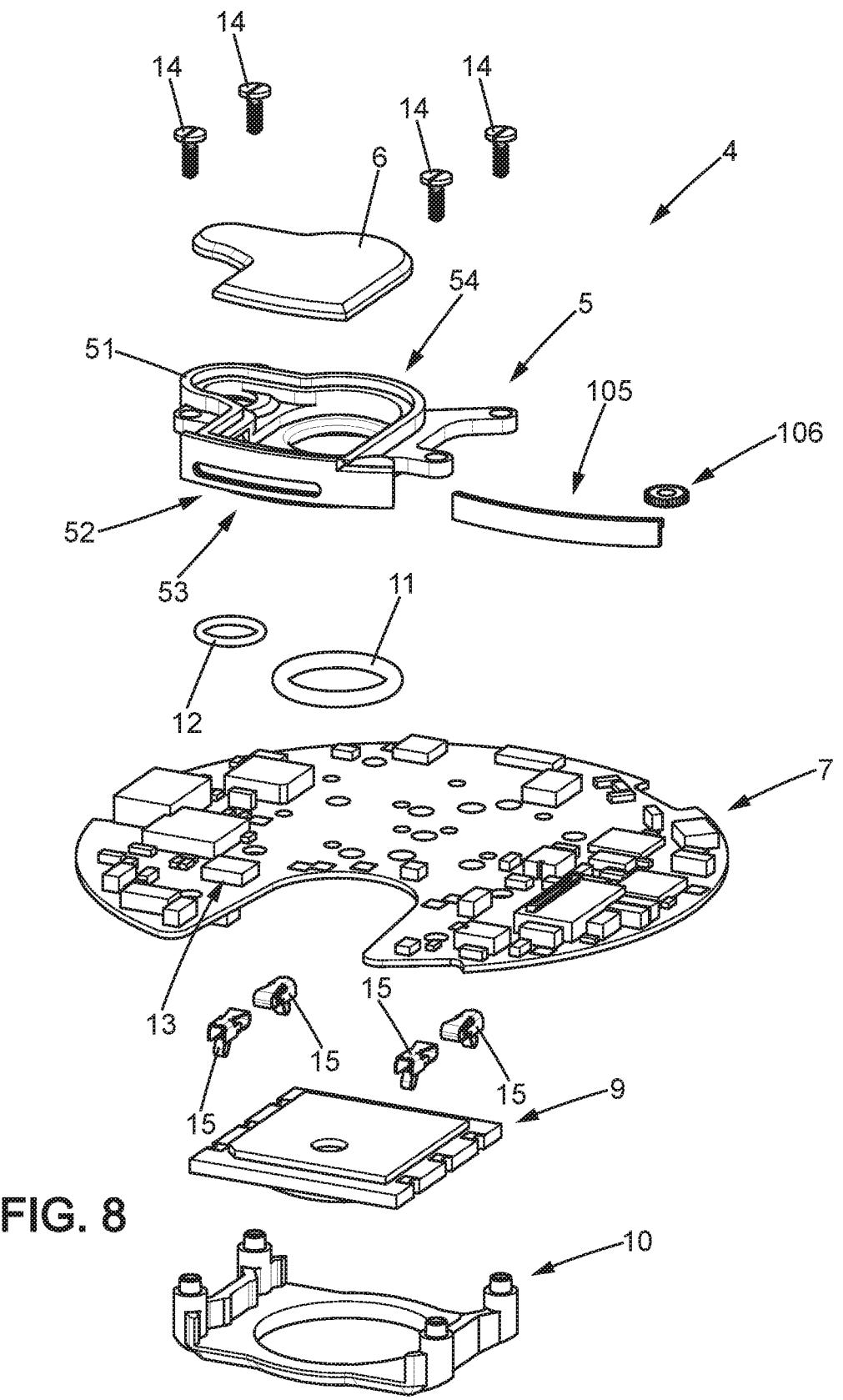
FIG. 8 shows an exploded view of the internal part of a device of FIG. 1 according to a second embodiment.

As illustrated on FIGS. 3 and 8, the device 1 comprises a humidity sensor 13 arranged in the cavity 5 of the internal part 4. The humidity sensor 13 is placed in the second hole 56 of the cavity 5. The humidity sensor 13 is sealed with the cavity 5 in an airtight manner with a gasket 12. The gasket 12 can seal the humidity sensor 13 with the cavity 5 in the same manner as the gasket 11 seals the air quality sensor 9 with the cavity 5.

Air can exclusively circulate between the outside and the inside of the cavity 5 through the opening 52, the cavity 5 being elsewhere isolated from the device 1. In particular, the cavity 5 is isolated from the other elements of the internal part 4 of the device 1, and more precisely from the other elements of the printed circuit board 7.

The air quality sensor 9 is adapted to measure a concentration of one or several air compounds in the vicinity of the device 1.

"In the vicinity of the device" means that the air compound(s) measured by the device 1 are not substantially different from the air compound(s) that the user of the device 1 is breathing or that surrounds the device 1.

The one or several air compounds are of interest. This way, the device 1 is adapted to detect compounds in the general environment of the device 1 and/or detect some chemical species present in the breath of the user when the user exhales or blows toward the device 1. The air quality sensor 9 is particularly suited to measure a concentration of some air compounds which may have an impact on human health (also called "pollutants").

The air quality sensor 9 may be adapted to measure a concentration of an air compound chosen among $NO_2$ (nitrogen dioxide), $O_3$ (ozone), NO (nitric oxide), CO (carbon monoxide), $SO_2$ (sulphur dioxide), $CO_2$ (carbon dioxide), $H_2S$ (hydrogen sulfide), CI (chlorine), benzene, CH4 (methane), $NH_4$ (ammonia), $(CH_3)_2CO$ (acetone) and alcohol vapours. The air compound can be a volatile organic compound.

When the air quality sensor 9 is used to detect some chemical species present in the breath of the user for instance, the air compound can be more precisely $NH_4$ (ammonia), $(CH_3)_2CO$ (acetone) and alcohol vapours.

The air quality sensor 9 may be adapted to measure a concentration of only one air compound or of several air compounds, in particular simultaneously. For instance, the air quality sensor 9 may be adapted to measure a concentration of two air compounds, such as those mentioned-above. The air quality sensor 9 may be reactive both to $NO_2$ and $O_3$.

According to an embodiment, the air quality sensor 9 can be an amperometric sensor. The air quality sensor 9 produces an electric current when a potential is applied between electrodes.

A first chemical occurs at least at one working electrode (or catalyst) when in contact with the air, which takes place with regard to at least one auxiliary electrode (or reference).

For example, if the air quality sensor 9 is adapted to measure a concentration of CO, the first chemical reaction may be:

$$CO+H_2O<=>CO_2+2e-+2H+ \text{ (electrons are released in the working electrode)}$$

According to another example, if the air quality sensor 9 is adapted to measure a concentration of $NO_2$, the first chemical reaction may be:

$$NO_2+2e-+2H+<=>NO+H_2O \text{ (electrons are captured in the working electrode)}$$

These chemical reactions are purely illustrative and non-limitative. More complex chemical reactions involving a larger number of chemical species are also possible.

Measurement of concentration of the air compound can also depend on other parameters, such as the ambient temperature, ambient humidity (more particularly measured by the humidity sensor 13 described above), ambient pressure or the electric intensity flowing through the air quality sensor 9.

Electrolyte may be provided between two or more electrodes to transport the ions produced by the chemical reactions from one electrode to the other electrode.

The air quality sensor 9 may have a low electric consumption, for example an average electric consumption when powered of less than 10 μA (microampere), or less than 2 μA. The electric current produced by the air quality sensor 9 can be comprised between 0.1 nA (nanoAmp) and 20 nA depending on the concentration of the air compound measured.

The lifetime of the battery of the device 1 can be sufficient to ensure a sufficiently long working life of the air quality sensor 9.

By way of example, the battery of the device 1 may have a capacity of 120 mAh (milliampere hour), with an autonomy of 25 days or 600 hours without using the air quality sensor 9. Its average electric consumption is 200 μA.

By considering that the average consumption of the air quality sensor 9 is 10 μA, the average electric consumption of the air quality sensor 9 is equal to 5% of the average electric consumption of the device 1 without using the air quality sensor 9. The device 1 may thus have an autonomy of around 24 days or around 570 hours when powering the air quality sensor 9.

The air quality sensor 9 is connected to the control unit of the device 1 which collects and processes the measurements of concentrations of the air compounds.

Such measurements can then be provided to the user, for instance on the display 31 of the device 1. As an alternative or complementarily, the device 1 may wirelessly communicate with another external terminal (not illustrated), such as a smartphone or a server, to send the collected measurement data.

Opening and Closing of the Cavity

Measurements made by the air quality sensor 9 can become out of calibration over time for a number or reasons.

For instance, external reasons, such as humidity and temperature, or internal reasons such as aging of components (e.g. electronic component, battery or coating material), may affect the accuracy of the air quality sensor 9.

It is therefore necessary to recalibrate the air quality 9 on a regular and/or periodic basis.

To this end, the cavity 5 can be alternatively in an open state or a closed state.

In the open state, air can enter into the cavity 5, so that the air present in the internal volume is constantly renewed from the outside of the cavity 5, and more particularly from the outside of the device 1.

In the closed state, no air can circulate between the outside and the inside of the cavity 5. The air present in the internal volume cannot be renewed and remains trapped in the cavity 5 as long as the cavity does not switch to the open state. The cavity 5 is hermetically sealed or airtight with respect to the air located outside the cavity 5, whether this air is located elsewhere inside the device 1 or outside the device 1.

In the closed state, concentration of the air compound can decrease over time, in particular since air cannot enter anymore into the cavity 5.

More precisely, the air quality sensor 9 is adapted to consume the air compound that is present in the internal volume of the cavity 5.

When the cavity 5 is in the closed state, the air quality sensor 9 can thus consume the entire air compound present in the internal volume of the cavity 5, so that the cavity 5 no longer comprises the air compound or comprises the air compound having a concentration that is below a predefined threshold, such as the detection threshold of the air quality device 9.

When the air compound is $NO_2$, such predefined threshold can be 5 ppb (parts per billion), 1 ppb or even 0.1 ppb.

For instance, the air quality sensor 9 can be adapted to measure the concentration of $NO_2$ according to the chemical reaction mentioned above, so that the air compound $NO_2$ can be progressively consumed by chemical reaction by the air quality sensor 9 when the cavity 5 is in the closed state, so that no $NO_2$ is finally left in the internal volume of the cavity 5 or only in trace amounts.

The air quality sensor 9 can consume the air compound in less than 8 hours, or in less than 4 hours, or in less than one hour, or even in less than 30 minutes. Consumption time of the air compound may depend on the air quality sensor parameters and on the size of the internal volume of the cavity 5.

To this end, the internal volume of the cavity 5 can be less than 0.3 cm$^3$ (cubic centimetre), less than 0.2 cm$^3$, less than 0.1 cm$^3$, or even less than 0.05 cm$^3$.

Then, the air quality sensor 9 can be calibrated. Calibration can encompass several possibilities, such as setting a new baseline measurement or the sensitivity of the air quality sensor 9. Calibration can also permit to obtain a calibration function in the form of a curve, a look-up table, or any other form in order to describe the linear or non-linear relation between the air compound concentration and the measurements to be performed by the air quality sensor 9.

Advantageously, the air quality sensor 9 can set a new baseline measurement (or a new "zero"). Every new measurement of the air quality sensor 9 can then be estimated by being compared with this new baseline measurement. This ensures a good reliability and accuracy of the air quality sensor 9 over time.

In particular, the air quality sensor 9 may be adapted to measure several air compounds but can be calibrated according to only one air compound.

When calibration is implemented, other parameters, such as the ambient temperature, ambient humidity, ambient pressure or the electric intensity flowing through the air quality sensor 9, may also be measured or set as reference values.

The material of the cavity 5 may also be advantageously chosen not to affect the measurements made by the air quality sensor 9. For instance, when the air quality sensor 9 is adapted to measure a concentration of $NO_2$, the cavity 5 may be made of polytetrafluoroethylene (PTFE).

We here below describe two embodiments of the cavity 5 so that it can be in the open or closed state.

First Embodiment of the Device

According to a first embodiment, the device 1 comprises a first grid 101 and a second grid 102. The first grid 101 is fixed relative to the cavity 5. In particular, the first grid 101 may be integral with the cavity 5. The first grid 101 is located at the inlet of, or forms, the opening 52 of the cavity 5.

The second grid 102 is adapted to move relative to the first grid 101 so that the cavity 5 can be in the open state or in the closed state. More precisely, the second grid 102 is adapted to slide relative to the first grid 101 along a longitudinal direction X1. The longitudinal direction X1 can be perpendicular to the vertical direction Z.

To move the second grid 102, the device 1 may comprise an actuator or motor (not illustrated) adapted to allow small displacements. The motor can for instance be piezoelectric, electromagnetic or it can be a stepper motor.

Each of the first and second grids 101, 102 comprises a plurality of through apertures 103, 104. The through apertures 103, 104 of the first and second grids 101, 102 are respectively spaced apart regularly in the longitudinal direction X1.

Figure 5A:
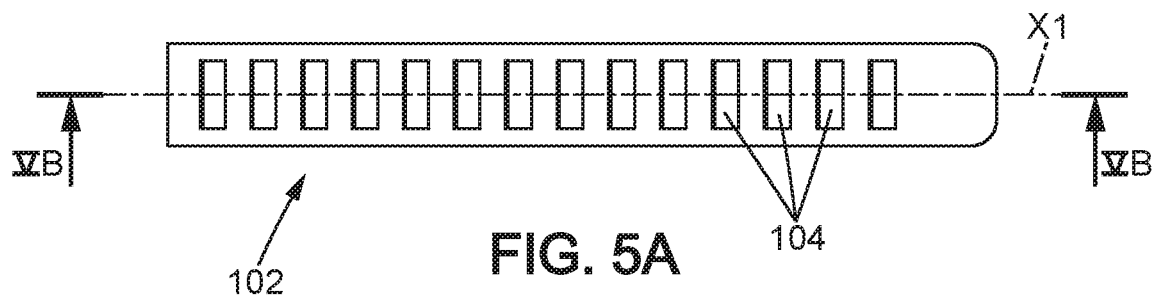
FIG. 5A shows front view of a second grid according to the first embodiment.
Figure 5B:
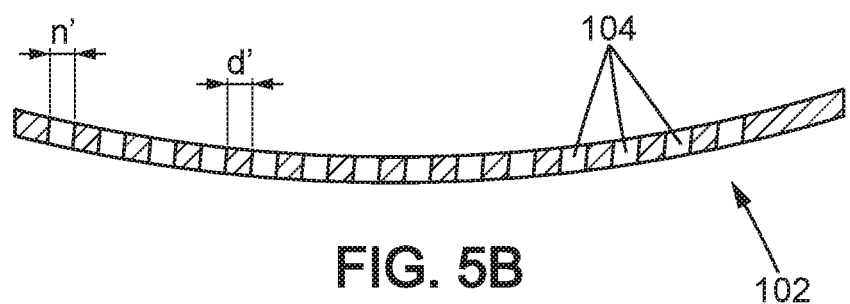
FIG. 5B shows a cross section of the second grid of FIG. 5A according to cross-sectional plane VB-VB.
Figure 6:
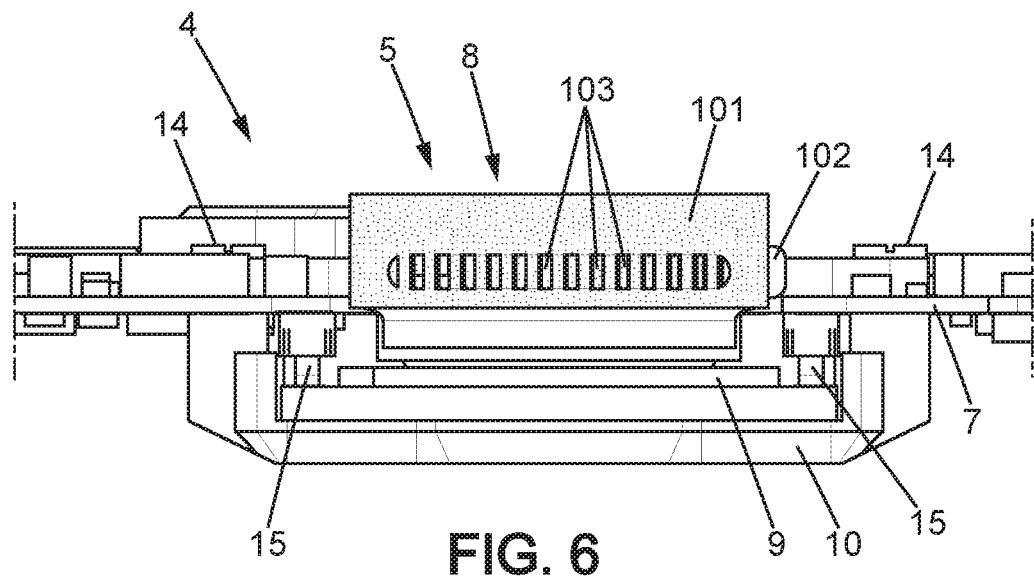
FIG. 6 shows a view of the cavity of FIG. 3 in which the cavity is in a closed state.
Figure 7:
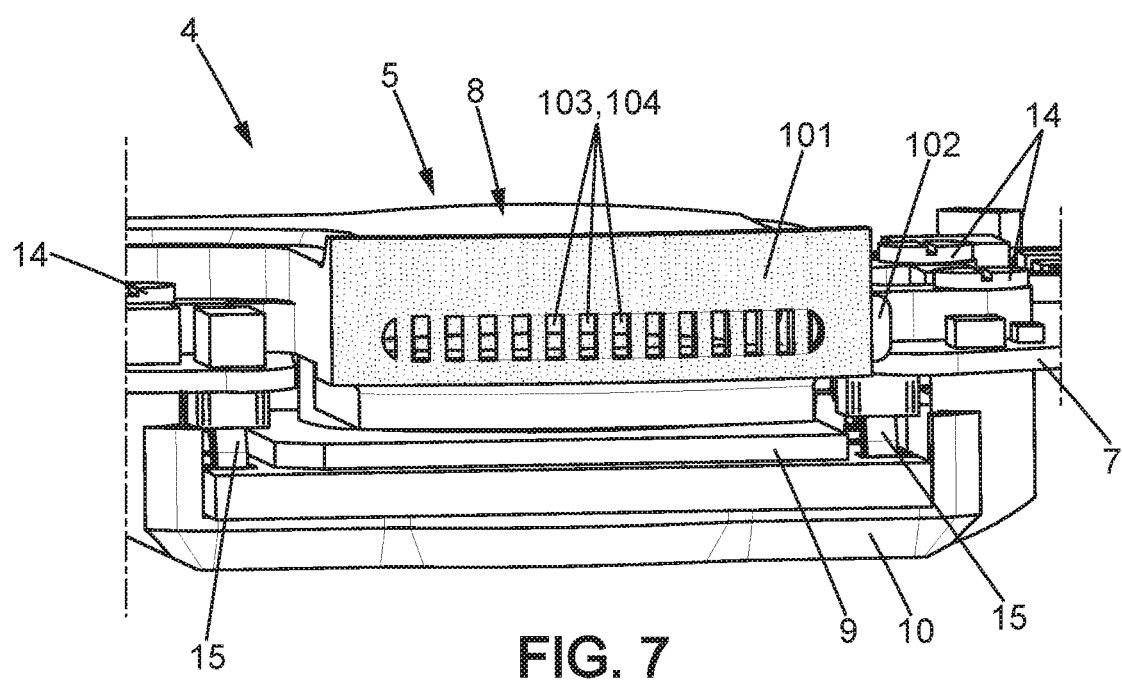
FIG. 7 shows a view of the cavity of FIG. 3 in which the cavity is in an open state.

As illustrated on FIGS. 4, 5A and 5B, each of the first and second grids 101, 102 comprises fourteen through apertures 103, 104. However, this is not limitative and the first and second grids 101, 102 can comprise less or more through apertures 103, 104.

The through apertures 103, 104 of the first and second grids 101, 102 can be of rectangular shapes. However, other shapes are possible.

As illustrated on FIG. 4, the through apertures 103 of the first grid 101 have a width n in the longitudinal direction X1. The width n of the through apertures 103 of the first grid 101 can be less than 1 mm (millimeter), or even less than 0.5 mm. The width n can be for instance equal to 0.3 mm.

The through apertures 103 of the first grid 101 are spaced apart regularly from each other by a distance d (also called "pitch").

Similarly, as illustrated on FIGS. 5A and 5B, the through apertures 104 of the second grid 102 have a width n' in the longitudinal direction X1. The width n' of the through apertures 104 of the second grid 102 can be less than 1 mm (millimeter), or even less than 0.5 mm. The width n' can be for instance equal to 0.3 millimeters. The through apertures 104 of the second grid 102 are spaced apart regularly from each other by a distance d'.

The widths n, n' and the distances d, d' are interrelated so that the cavity 5 can be opened or closed in a satisfactory manner by moving the second grid 102 relative to the first grid 101

Advantageously, the first and second grids 101, 102 are such that:

$n' \geq n,$

This way, in the open position, a through aperture 104 of the second grid 102 overlaps totally a though aperture 103 of the first grid 101. All or some of the though apertures 103, 104 face each other. The cavity 5 is thus open as illustrated on FIG. 7.

Advantageously, the first and second grids 101, 102 are such that:

$d' \geq n$ and $d \geq n'$

This way, in the closed position, the solid space between two consecutive through apertures 104 of the second grid 102 overlaps totally, or covers, a through aperture 103 of the first grid 101. Similarly, the solid space between two consecutive through apertures 103 of the first grid 101 overlaps totally, or covers, a through aperture 104 of the second grid 102. The through apertures 103, 104 of the first and second grids 101, 102 are offset to one another in the longitudinal direction X1. The cavity 5 is thus totally closed as illustrated on FIG. 6.

Second Embodiment of the Device

According to a second embodiment, the device 1 comprises a door 105. The door 105 is adapted to move relative to the opening 52 so that the cavity 5 can be in the open state or in the closed state. More precisely, the door 105 is adapted to slide relative to the opening 52 along a longitudinal direction X2. The opening 52 may consist in a single aperture which extends in the longitudinal direction X2.

Figure 13:
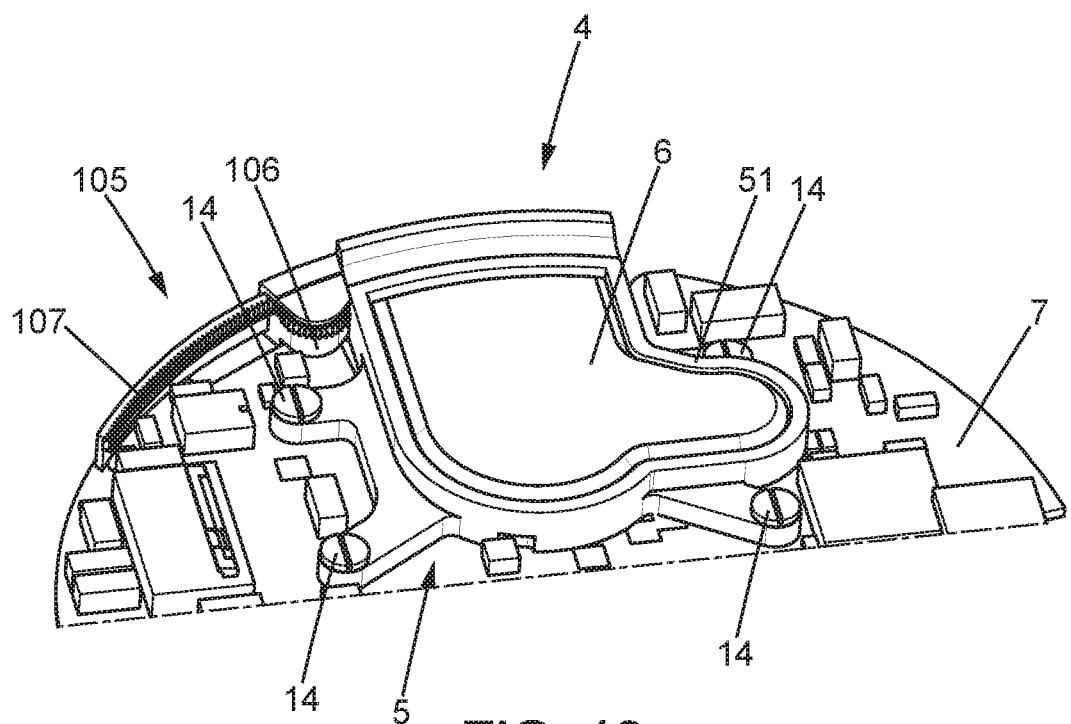
FIG. 13 shows a perspective top view of the internal part of FIG. 12.

To move the door 105, the device 1 may comprise a toothed disk or a pinion 106. The door 105 comprises a rack 107 that can engage with the toothed disk 106, as illustrated more particularly on FIG. 13.

The door 105 is a full solid surface, which does not comprise any through apertures unlike the second grid 102 of the first embodiment described above.

Figure 11:
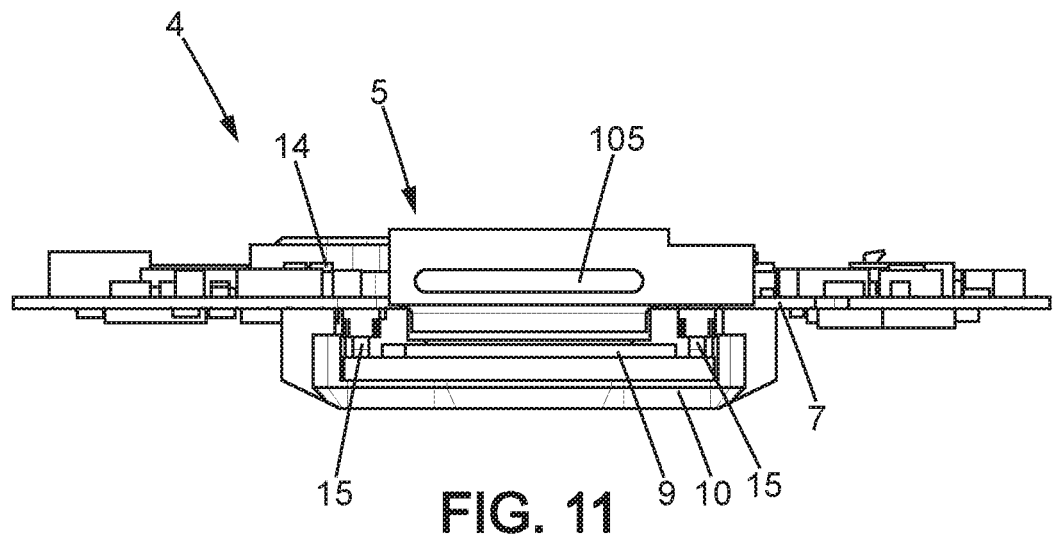
FIG. 11 shows a view of the cavity of FIG. 8 in which cavity is in a closed state.

In the closed state, the door 105 faces the opening 52. The cavity 5 is thus totally closed as illustrated on FIG. 11.

Figure 12:
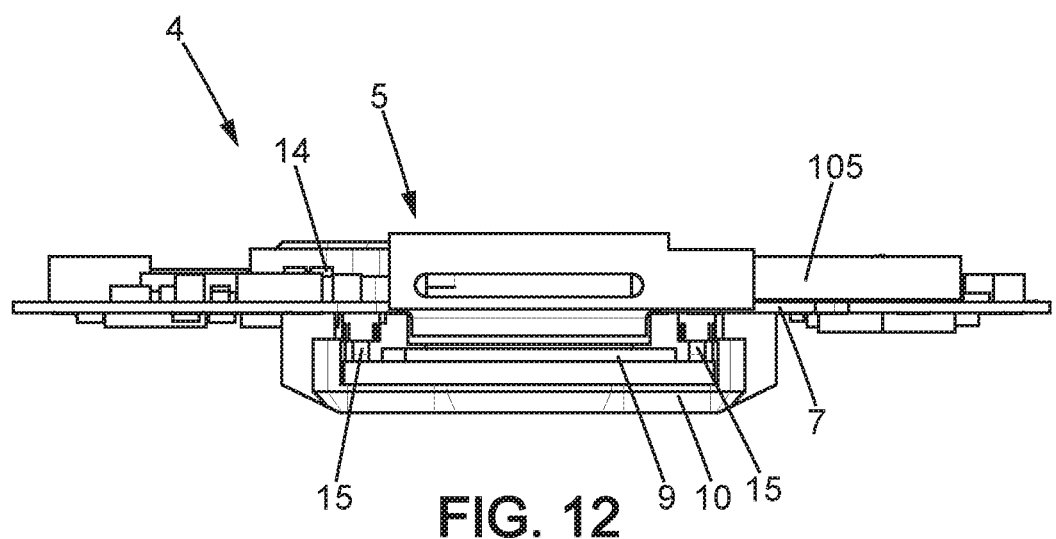
FIG. 12 shows a view of the cavity of FIG. 8 in which the cavity is in an open state.

In the open state, the door 105 does not cover the opening 52 by being slidably moved, preferably totally, on a side of the opening 52 along the longitudinal direction X2. The cavity 5 is thus open as illustrated on FIG. 12.

Advantages of the Disclosure

Thanks to the fact that the cavity 5 can switch from the open state to the closed state, it is possible to recalibrate the air quality sensor 9 when the air compound to be measured has been totally, or almost totally, consumed in the internal volume.

This calibration is advantageously implemented when the user is unlikely to use the device 1 as well as the embedded air quality sensor 9 for a given period of time.

To this end, the device 1 may also comprise a biosensor of a physiological signal of the user, such as an accelerometer (not illustrated) adapted to detect a movement of the user. Calibration of the air quality sensor 9 can then be implemented when the biosensor does not detect any activity of the user, and in particular when the accelerometer does no detect any movement of the user.

Such calibration can for instance occur during a sleeping phase of the user or, in the embodiment wherein the device 1 is a wearable device, when the device 1 is not worn by the user.

Such calibration can also be repeated in a periodic manner. For instance, such calibration can occur at least once a month, or at least once a week, or even at least once a day. This way, it ensures that the air quality sensor 9 always output a reliable measurement of the concentration of the air compound.

Obviously, the disclosure is not limited to the embodiments described previously and given purely by way of example. It encompasses a wide range of modifications, alternative forms and other variants that a person skilled in the art will be able to envisage within the scope of the present disclosure and notably all combinations of the different modes of operation described previously, being able to be taken separately or together.

The invention claimed is:

1. A device comprising a housing delimiting a cavity having an internal volume, an air quality sensor being adapted to measure a concentration of at least one air compound present in the internal volume, and a movable member configured to be moved by an actuator between an open position and a closed position,
wherein the housing can be alternatively in:
an open state in which the movable member is in the open position and air can enter into the cavity from an outside area of the housing, and
a closed state in which the movable member is in the closed position and no air can circulate between the outside area of the housing and an inside area of the housing, wherein the air quality sensor consumes the air compound that is present in the internal volume such that the concentration of the air compound decreases over time since air cannot enter into the cavity in the closed state,
the air quality sensor being adapted to be calibrated when the housing is in the closed state and once the internal volume no longer comprises the air compound or comprises a concentration of the air compound that is below a predefined threshold.

2. The device according to claim 1, wherein the housing comprises an opening so that air can exclusively enter or leave the cavity through the opening, the internal volume being elsewhere isolated from the device.

3. The device according to claim 2, wherein the movable member is formed as a door, the door being adapted to be moved relative to the opening so that the housing can be selectively in the open state or in the closed state.

4. The device according to claim 2, further comprising a membrane which is impermeable to water but permeable to air, the membrane being placed in front of the opening at the outside of the housing.

5. The device according to claim 1, wherein the air quality sensor is adapted to produce an electric current by consuming the air compound present in the internal volume.

6. The device according to claim 1, wherein the air compound is $NO_2$.

7. The device according to claim 1, wherein the internal volume of the cavity is less than $0.3$ cm$^3$, less than $0.2$ cm$^3$, less than $0.1$ cm$^3$, or even less than $0.05$ cm$^3$.

8. The device according to claim 1, wherein the housing comprises a first grid and the movable member is formed as a second grid, the second grid being adapted to be moved relative to the first grid so that the housing can be selectively in the open state or in the closed state.

9. The device according to claim 8, wherein each of the first and second grids comprises a plurality of through apertures, wherein at least some of the through apertures of the first and second grids face each other when the housing is in the open state and wherein the through apertures of the first and second grids are offset to one another when the housing is in the closed state.

10. The device according to claim 1, comprising an accelerometer adapted to detect a movement of a user of the device, the air quality sensor being adapted to be calibrated when the accelerometer does not detect any movement of the user of the device.

11. The device according to claim 1, wherein the housing comprises a hole, the air quality sensor being in fluid communication with the internal volume via the hole, the housing and the air quality sensor being sealed together in an airtight manner by using at least one gasket.

12. The device according to claim 1, wherein the device is a wearable device configured to be attached to the wrist of user.

13. The device according to claim 1, wherein the movable member is configured to be slidably moved between the open position and the closed position.

14. A method for calibrating an air quality senor of a device, the device comprising a housing delimiting a cavity having an internal volume, the air quality sensor being adapted to measure a concentration of at least one air compound present in the internal volume, and a movable member configured to be moved by an actuator between an open position and a closed position, the housing being alternatively in an open state in which the movable member is in the open position and air can enter into the cavity from the outside of the housing, and a closed state in which the movable member is in the closed position and no air can circulate between an outside area of the housing and an inside area of the housing,
the method comprising:
switching the housing from the open state to the closed state;
waiting, while the air quality sensor consumes the air compound that is present in the internal volume, for the internal volume to no longer comprise the air compound or to comprise a concentration of the air compound that is below a predefined threshold; and
calibrating the air quality sensor.

15. A method for calibrating an air quality sensor of a device, the device comprising a housing delimiting a cavity having an internal volume, the air quality sensor being adapted to measure a concentration of at least one air compound present in the internal volume, and a movable member configured to be moved by an actuator between an open position and a closed position,
the housing being alternatively in an open state in which the movable member is in the open position and air can enter into the cavity from the outside of the cavity, and a closed state in which the movable member is in the closed position and no air can circulate between an outside area of the housing and an inside area of the housing,
the method comprising:
moving the movable member from the closed position to the open position such that the housing is switched from the open state to the closed state;
waiting a predetermined duration, while the air quality sensor consumed the air compound that is present in the internal volume, such that the internal volume comprises a concentration of the air compound below a predefined threshold; and
calibrating the air quality sensor.

* * * * *